United States Patent [19]

Bigi

[11] 4,115,259

[45] Sep. 19, 1978

[54] METHOD FOR REGENERATING DIALYSING LIQUIDS IN HEMODIALYSIS SYSTEMS

[76] Inventor: Leonardo Bigi, Via S. Giovanni, 15, Mirandola (Modena), Italy

[21] Appl. No.: 685,024

[22] Filed: May 10, 1976

[51] Int. Cl.$^2$ .............................................. B01D 13/00
[52] U.S. Cl. ................................. 210/22 A; 210/321 B
[58] Field of Search ................. 210/22, 321 R, 321 B, 210/259; 195/63, 68, DIG. 11; 252/455 R

[56] References Cited

U.S. PATENT DOCUMENTS

| | | | |
|---|---|---|---|
| 2,409,494 | 10/1946 | Keating | 252/430 |
| 3,703,959 | 11/1972 | Raymond | 210/321 B |
| 4,036,747 | 7/1977 | Hori et al. | 210/22 A |

OTHER PUBLICATIONS

Transactions "American Society for Artificial Internal Organs" pp. 446–449, vol. XIX, 1973.

*Primary Examiner*—Frank A. Spear, Jr.
*Assistant Examiner*—E. Rollins Cross
*Attorney, Agent, or Firm*—Guido Modiano; Albert Josif

[57] ABSTRACT

A method for removing phosphate ions from spent dialysing liquids used in hemodialysis consisting of contacting the liquid with an activated mixture of alumina and silica. The activation treatment consists of a roasting at a temperature in the range of 300°–800° C.

7 Claims, 1 Drawing Figure

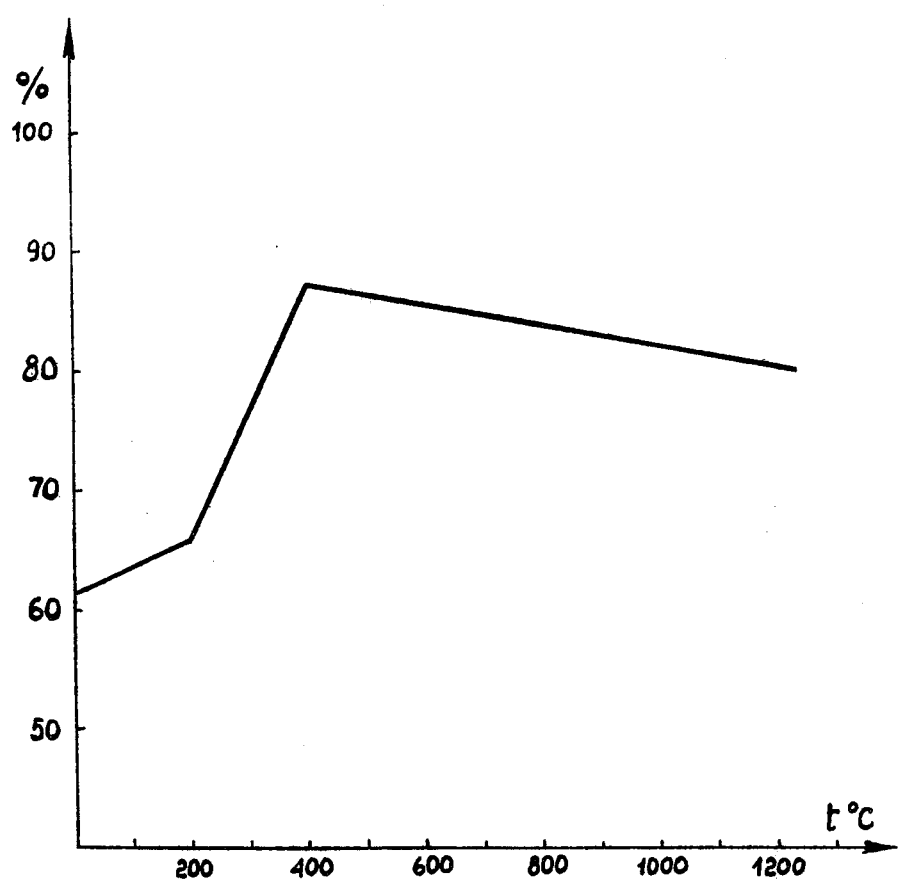

METHOD FOR REGENERATING DIALYSING LIQUIDS IN HEMODIALYSIS SYSTEMS

BACKGROUND OF THE INVENTION

This invention relates to a method for purifying dialysing liquids used in hemodialysis processes. In particular the invention relates to the removal of phosphate ions from these dialysing liquids.

Hemodialysis processes, i.e. processes for purifying human blood by dialysis, have recently been studied in which the dialysing liquid is continuously recycled after passing through a purification or regeneration stage. In the regeneration stage the toxins originating from the blood, the most important of which are urea, ureic acid, creatinine etc. are removed from the dialysing liquid. Although the presence of phosphate ions is also harmful to the human body, the removal of these ions has been relatively ignored in the dialysing liquid regeneration methods used up to the present time.

The need to remove phosphate ions from the blood derives from the fact that these ions displace the calcium and magnesium from the body to a harmful level, giving rise to the dangerous phenomenon of decalcification of the osseous system. As the proper transfer of phosphate ions from the blood to the dialysing liquid is dependent upon low concentration of these ions in this latter, it is necessary to remove substantially 80% of the phosphate ions from the dialysing liquid before recycling it to the hemodialysis process.

In known dialysing liquid purification processes the phosphate ions have been eliminated by absorption on activated carbon, together with other toxins of an organic nature. The main disadvantage of these methods is the poor capacity of activated carbon to retain the phosphate ions. It has been attempted to replace the activated carbon by other absorbents more effective in removing phosphate ions, such as zirconium oxide. These absorbents however have been shown to be just as disadvantageous in that in addition to the phosphate they remove substantial quantities of calcium, magnesium and potassium ions, so destroying the required electrolytic equilibrium of the dialysing liquid. It is therefore necessary in such purification systems to continuously infuse calcium, magnesium and possibly potassium into the dialysing liquid before recycling it to the dialysis process.

However these requirements lead to considerable clinical complications, and make the entire hemodialysis process difficult to carry out.

SUMMARY OF THE INVENTION

The main object of the present invention is to provide a method for removing phosphate ions from dialysing liquids used in hemodialysis processes, which gives effective phosphate removal of the required level.

A further object of the invention is to provide a method for removing only phosphate ions from the dialysing liquid, leaving the other salts providing the electrolytic equilibrium of the dialysing liquid almost intact.

A further object of the present invention is to provide a simple, effective and economical method for regenerating dialysing liquids in hemodialysis processes.

These and further objects which will be more evident hereinafter are attained by a method for removing phosphate ions particularly from dialysing liquids in hemodialysis processes, consisting of bringing the dialysing liquid into contact with a mixture of a preavailing amount of aluminium oxide and a minor amount of silicon oxide activated by roasting at a temperature in the range 300°–800° C, and separating said dialysing liquid substantially free from phosphate ions.

BRIEF DESCRIPTION OF THE DRAWING

In the accompanying drawing FIG. 1 shows a graph illustrating on the ordinate the variation (as a percentage) in the phosphorus removed from a dialysing liquid by the present method, as a function of the temperature ($t°$ C), represented on the abscissa, used during the activation treatment.

DESCRIPTION OF THE PREFERRED EMBODIMENT

The method of the present invention is based on the surprising discovery that a mixture of aluminium and silicon oxides activated in the aforementioned manner eliminates only the harmful phosphate ions removed from the dialysed blood, and has little activity towards other ions such as Na, K, Ca, Mg, Cl, which provide the required electrolytic equilibrium of the dialysing liquid.

The absorbent used in the method of the present invention may either be prepared by mixing the individual aluminium and silicon oxides in the required proportions or be a preformed mixture of these oxides available commercially. It has been found that excellent results in terms of phosphate removal are obtained with mixtures of alumina and silica in which 85–95% of the mixture is alumina.

Preferably the starting material used in Porocel O, which is the trademark of a commercially obtainable mineral having an average chemical composition of 6% $SiO_2$ and 91% $Al_2O_3$, the remainder being iron and titanium oxides.

In a preferred embodiment of the method of the present invention, the roasting is carried out in two stages.

The starting mixture of oxides is firstly subjected to dust removal and washing with deionised water, and then dried at about 70° C, followed by a first roasting stage at a temperature in the range of 300°–800° C for a period of about 5 hours.

The oxide mixture is then put into contact with a solution of calcium salts. In this manner the secondary absorption selectivity of the aluminium and silicon oxide mixture towards $Ca^{++}$ ions, representing a disturbance selectivity, is completely eliminated while the selectivity towards $Mg^{++}$ ions, which within certain limits is desirable, is increased. The contact is for about 30–60 minutes.

The oxide mixture is again dried and subjected to a second roasting stage at a temperature in the range of 300°–800° C.

It has been found that optimum results with regard to the capacity of the oxide mixture for selectively absorbing phosphate ions are obtained in this temperature range when both the first and second roasting stage are carried out at around 400° C. In this respect, as shown on the graph of FIG. 1 (obtained putting into contact 100 ml of physiological solution containing $Na_2HPO_4$ and having a pH of 7.4 with 1g of the oxide mixture activated at various temperatures), the curve representing the amount of phosphorous removed as a percentage of the total phosphorous in a dialysing liquid has a maximum value at a roasting temperature of the oxide mixture of 400° C. By this treatment a porous material is obtained which surprisingly shows excellent activity in removing phosphate ions from the dialysing liquid. This material, besides behaving towards $Ca^{++}$ and $Mg^{++}$ ions as heretofore stated, also remains inert towards the other ions contained in the dialysing liquid such as sodium and potassium.

Advantageously, the mixture of aluminium and silicon oxides according to the invention provides the dialysing liquid with a desirable reserve of alkaline pH. This alkaline reserve is useful as it enables the patient, who begins dialysis in a marked acidosis state, to be brought to a pH in the required physiological pH range of 7.4–7.8.

Advantageously the method for removing phosphate ions according to the present invention may be combined with a dialysing liquid regeneration process comprising additional stages for removing other toxins derived from the blood such as urea, creatinine, ureic acid, methyl guanidine, etc.

From the description given heretofore it is seen that the phosphate ion removal process of the present invention attains the predetermined objects.

In this respect, the method ensures effective elimination of the phosphate ions without damaging the required electrolytic equilibrium of the dialysing liquid.

The need to infuse ions such as calcium, magnesium and potassium is avoided, so considerably simplifying the process and making it more economical.

The following example illustrates a preferred embodiment of the invention.

EXAMPLE

In a purifying cartrige a bed of a base diameter of 84 mm and a height of 100 mm was formed with 500 g. of an oxide mixture consisting of Porocel O (91% $Al_2O_3$ and 6% $SiO_2$) activated by a roasting at 400° C.

Spent dialysing liquid was passed through this bed at a flow rate of 500 ml/min and temperature of 41° C. In an operating period of 5 hours a removal of phosphate ions of 99% by weight of the initial phosphate contents of the liquid was obtained.

I claim:

1. A method for removing phosphate ions particularly from dialysing liquids used in hemodialysis processes, consisting of bringing the dialysing liquid into contact with a mixture having a major proportion of aluminium oxide and a minor proportion of silicon oxide wherein said mixture is free from gel-type alumina and is activated by roasting at a temperature in the range of from 300° to 800° C, and separating said dialysing liquid substantially free from phosphate ions.

2. A method as claimed in claim 1, wherein said roasting is carried out at 400° C for a period of 5 hours.

3. A method as claimed in claim 1, wherein said roasting is carried out in two stages, between which said oxide mixture is subjected to further treatment consisting of bringing said mixture into contact with a solution of calcium salts.

4. A method as claimed in claim 1, wherein said oxide mixture comprises 85–95% by weight of $Al_2O_3$ and, correspondingly, 15–5% by weight of $SiO_2$.

5. A process as claimed in claim 1, wherein said oxide mixture consists of Porocel comprising 6% of $SiO_2$ and 91% of $Al_2O_3$, the remainder being iron and titanium oxides.

6. A method for regenerating dialysing liquids used in hemodialysis processes, comprising a phosphate ion removal stage effected by a method as claimed in claim 1.

7. A method for removing phosphate ions particularly from dialysing liquids used in hemodialysis processes consisting in bringing the dialysing liquid into contact with a mixture having a major proportion of aluminium oxide and a minor proportion of silicon oxide wherein said mixture is free from gel-type alumina, said mixture being treated by roasting it at a temperature in the range of from 300° to 800° C and bringing it into contact with a solution of calcium salts, and separating said dialysing liquid substantially free from phosphate ions.

* * * * *